(12) United States Patent
Hirai et al.

(10) Patent No.: US 9,982,014 B2
(45) Date of Patent: May 29, 2018

(54) TETRAPEPTIDE COMPOUND AND METHOD FOR PRODUCING SAME

(71) Applicants: Kaneka Corporation, Osaka (JP); Stealth Bio Therapeutics Corp, Monaco (MC)

(72) Inventors: Yoshinori Hirai, Takasago (JP); Akira Nishiyama, Takasago (JP); Masaru Mitsuda, Takasago (JP)

(73) Assignees: Kaneka Corporation, Osaka (JP); Stealth BioTherapeutics Corp, Monaco (MC)

( * ) Notice: Subject to any disclaimer, the term of this patent is extended or adjusted under 35 U.S.C. 154(b) by 0 days. days.

(21) Appl. No.: 15/031,135

(22) PCT Filed: Oct. 23, 2014

(86) PCT No.: PCT/JP2014/078840
§ 371 (c)(1),
(2) Date: Apr. 21, 2016

(87) PCT Pub. No.: WO2015/060462
PCT Pub. Date: Apr. 30, 2015

(65) Prior Publication Data
US 2016/0264623 A1    Sep. 15, 2016

(30) Foreign Application Priority Data

Oct. 23, 2013   (JP) ................. 2013-220655

(51) Int. Cl.
| A61K 38/00 | (2006.01) |
| A61K 38/07 | (2006.01) |
| C07K 5/113 | (2006.01) |
| C07K 5/11  | (2006.01) |

(52) U.S. Cl.
CPC .......... C07K 5/1021 (2013.01); C07K 5/1019 (2013.01); *A61K 38/00* (2013.01); *C07B 2200/13* (2013.01)

(58) Field of Classification Search
CPC .... A61K 38/00; A61K 38/07; C07B 2200/13; C07K 5/1019; C07K 5/1021; C07K 5/07

USPC .......................................... 530/330; 514/21.9
See application file for complete search history.

(56) References Cited

FOREIGN PATENT DOCUMENTS

| EP | 2 436 390 | 4/2012 | |
| JP | H05-255105 | 10/1993 | |
| JP | H08-503475 | 4/1996 | |
| JP | 2007-518818 | 7/2007 | |
| JP | 2009-544712 | 12/2009 | |
| WO | WO-99/18948 | 4/1999 | |
| WO | WO-00/12539 | 3/2000 | |
| WO | WO-2007/022459 | 2/2007 | |
| WO | WO-2009/113320 | 9/2009 | |
| WO | WO-2011/139992 A1 | 11/2011 | |
| WO | WO-2013/086020 | 6/2013 | |
| WO | WO 2015/197723 | * 12/2015 | ............... C07K 5/11 |

OTHER PUBLICATIONS

Nozawa et al., "Identification of Arginine Analogues as Antagonists and Agonists for the Melanocortin-4 Receptor," Chem. Pharm. Bull 55(8) 1232-1239, 2007.
International Search Report for PCT/JP2014/078840 dated Dec. 22, 2014.
Written Opinion for PCT/JP2014/078840 dated Dec. 22, 2014.
Sellers et al., "Design and synthesis of Hsp90 inhibitors: Exploring the SAR of Sansalvamide A derivatives," Bioorganic & Medicinal Chemistry, 18, 2010, 6822-6856.
"Novabiochem(R) Guide to selection of building block," Merck, Copyright 2012.
Isidro-Llobet et al., "Amino Acid-Protecting Groups," American Chemical Society, Chemical Reviews, 2009, vol. 109, No. 6.
Wuts et al., "Greene's Protective Groups in Organic Synthesis," Fourth Edition, 2007, pp. 696-707.

* cited by examiner

*Primary Examiner* — Julie Ha
(74) *Attorney, Agent, or Firm* — James P. McParland; Foley & Lardner LLP

(57) ABSTRACT

The present invention is to provide a method for the efficient production on an industrial scale of SS-31 (D-Arg-Dmt-Lys-Phe-NH$_2$), which is an SS peptide. According to the present invention, the desired SS-31 is produced by efficiently synthesizing a tetrapeptide compound as a precursor of SS-31 and improving the tetrapeptide purity by crystallization.

11 Claims, 2 Drawing Sheets

TETRAPEPTIDE COMPOUND AND METHOD FOR PRODUCING SAME

CROSS-REFERENCE TO RELATED APPLICATIONS

This application is the U.S. 371 National Stage Application of International Application No. PCT/JP2014/078840, filed Oct. 23, 2014, which claims the benefit of and priority to Japanese Application No. 2013-220655, filed Oct. 23, 2013, the contents of which are incorporated herein by reference in their entireties.

TECHNICAL FIELD

The present invention relates to a novel tetrapeptide compound that is important in the production of one of the SS-peptides, SS-31 (D-Arg-Dmt-Lys-Phe-NH$_2$), and a method for producing the same. Moreover, the present invention relates to a method for producing SS-31 using the tetrapeptide compound.

BACKGROUND

SS-peptides (Szeto-Schiller Peptides) are peptides that have antioxidant activity in mitochondria and are being developed for use in pharmaceutical drugs (patent documents 1 and 2).

The method whereby a peptide is synthesized by conventional solid-phase synthesis from a commercial amino acid derivative and cut from the resin, and then the untreated peptide is purified by preparative liquid-phase chromatography (patent document 1) is known as a method for producing one of the SS-peptides, SS-31 (D-Arg-Dmt-Lys-Phe-NH$_2$). Nevertheless, the solid-phase synthesis of a peptide and purification by preparative liquid-phase chromatography are not suited to an industrial scale and therefore, mass synthesis of SS-31 by the above-mentioned production method is difficult.

On the other hand, the following peptides having intramolecular Arg(Z)2 are known as intermediates of peptide synthesis:

(1) Dipeptide: 2-(R)-(2-(4-(1-n-propyl)phenyl)ethyl)-1,5-pentanedioic acid 1-(1-arginine, N-methylamide)amide is obtained as a colorless solid by silica gel column chromatography purification (patent document 4).

(2) Dipeptide: (R)—N,N-bis(Cbz)-N-diphenylacetyl-(R)—N-[1-(4-hydroxyphenyl)-ethyl]arginine amide is obtained as a white powder by silica gel column chromatography (methylene chloride/ethyl acetate) purification (patent document 5).

(3) Tripeptide: Boc-D-Arg(Z)2-Phe-MeβAla-OPac is obtained as a white solid by silica gel column chromatography (chloroform/methanol=100/1) purification followed by crystallization from hexane (patent document 6).

(4) Tripeptide: Boc-D-2-Nal-Arg(Z)2-2-Nal—NH2 is obtained as a solid by silica gel column chromatography (chloroform/methanol=50/1) purification followed by crystallization from ethyl acetate (non-patent document 1).

(5) Tetrapeptide: Boc-Arg(Z)2-Gly-Asp(Bn)-Ser(Bn)-OBn is obtained as a white powder by silica gel column chromatography (chloroform/methanol=99/1) purification (patent document 3).

(6) Tetrapeptide: [4-tert-butyl-2 (R)-[3-(4-methoxyphenyl)propyl]succinyl]-L-tryptophan-L-alanine-L-N,N-bis(benzyloxycarbonyl)arginine-N-methylamide is obtained as a milky white solid by silica gel column chromatography (chloroform/methanol=200/1) purification (patent document 7).

(7) Pentapeptide: MeO-D-Trp-Leu-Val-Arg(Z)2-Val-NH-Boc is obtained by silica gel column chromatography (ethyl acetate/hexane) purification (non-patent document 2).

As described above, a peptide having intramolecular Arg(Z)2 is generally purified by silica gel column chromatography. There are almost no examples of successful crystallization. Taking into consideration the purity required of a peptide product, silica gel column chromatography is indispensable at the present time.

PATENT DOCUMENTS

[Patent document 1] JP (Kohyo) 2007-518818
[Patent document 2] JP (Kohyo) 2009-544712
[Patent document 3] JP (Kokai) H05-255105
[Patent document 4] JP (Kohyo) H08-503475
[Patent Document 5] International Publication No. WO1999/18948
[Patent Document 6] International Publication No. WO 2000/12539
[Patent Document 7] International Publication No. WO2009/113320

Non-Patent Documents

[Non-Patent Document 1] Chem. Pharm. Bull. 2007, 55(8), 1232-1239.
[Non-Patent Document 2] Bioorg. Med. Chem. 2010, 18, 6822-6856.

SUMMARY OF INVENTION

In light of the problems of the above-mentioned prior art, the problem to be solved by the present invention is providing a production method with which high-purity SS-31 can be simply and efficiently produced on an industrial scale.

As a result of concerted research, the inventors successfully perfected the present invention upon discovering a method for producing the desired SS-31 at a high purity by efficiently synthesizing a novel tetrapeptide compound, improving purity by further crystallization of the novel tetrapeptide compound, and using the resulting tetrapeptide as the SS-31 precursor.

That is, the present invention is a tetrapeptide compound represented by the following formula (1)

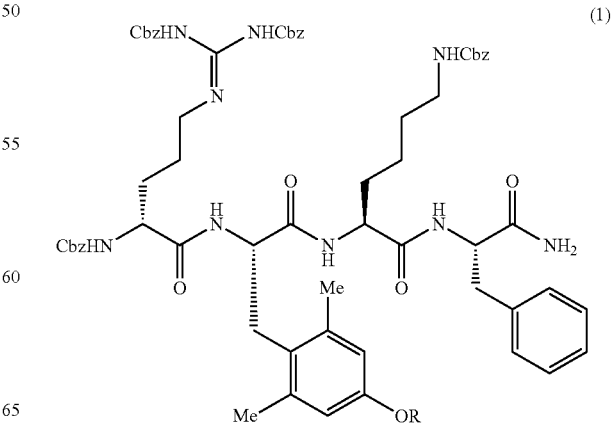

(where R is a hydrogen atom, benzyl group, or benzyloxycarbonyl group).

Those of skill in the art will appreciate that compounds of the present technology may exhibit the phenomena of tautomerism. As the formula drawings within the specification and claims can represent only one of the possible tautomeric forms, it should be understood that the present technology encompasses any tautomeric form of the compounds described herein, as well as mixtures thereof.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, guanidine may exhibit the following isomeric forms, which are referred to as tautomers of each other:

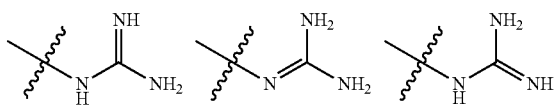

Similarly, bis-protected guanidine may also exhibit tautomers:

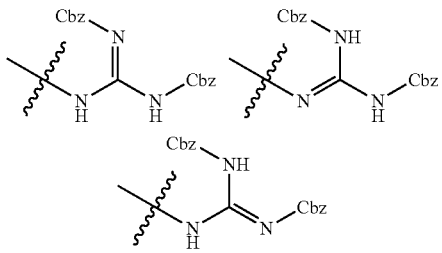

As readily understood by one skilled in the art, a wide variety of functional groups and other structures may exhibit tautomerism, and all tautomers of compounds described herein are within the scope of the present technology.

The present technology further provides the tetrapeptide compound of formula (1) as a crystalline solid having one, two, three or more of the following peaks at $2\lambda \pm 0.1$ of 5.4°, 5.8°, 8.4°, 10.5°. 10.9°, 11.8°, 13.1°, 13.4°13.6°, 14.3°, 15.6°, 16.3°, 17.1°, 17.6°, 18.0°, 18.6°, 19.1°, 20.1°, 20.6°, 21.9°, 22.1°, 22.8°, 23.6°, 23.8°, 24.9°, 25.3°, 26.2°, 26.4°, 29.0°, 29.2°, and 29.4° in a powder X-ray diffraction spectrum obtained using Cu—Kα radiation. In some embodiments, the crystalline tetrapeptide of formula (1) exhibits one or more, (e.g., two, three, four, five, six, seven, or eight) peaks at $2\theta \pm 0.1$ selected from 5.4°, 10.5°, 15.6°, 17.6°, 18.0°, 18.6°, 20.1°, and 20.6°.

Moreover, the present invention is a method for producing a peptide pharmaceutical, characterized in that the tetrapeptide compound represented by the following formula (1)

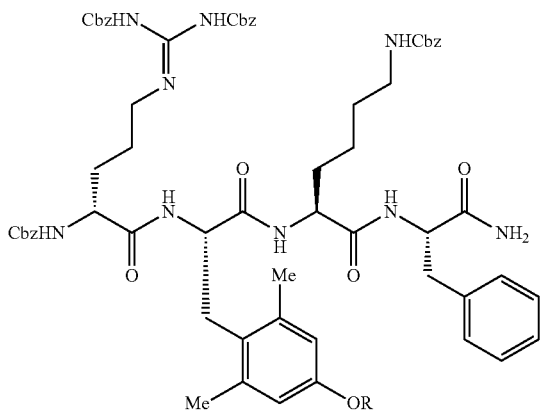

(where R is a hydrogen atom, benzyl group, or benzyloxycarbonyl group) is catalytically reduced to produce a peptide pharmaceutical represented by the following formula (2).

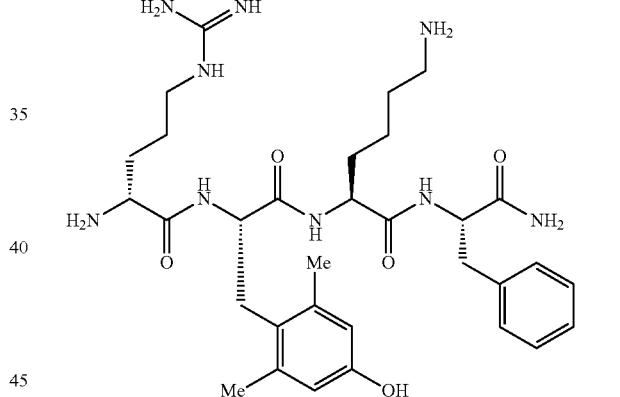

Effect of Invention

By means of the present invention, it is possible to easily and efficiently produce a highly-pure SS-31 on an industrial scale. In some embodiments, "on an industrial scale" means on a scale greater than 1 g, greater than 5 g, greater than 10 g, greater than 50 g, greater than 100 g, greater than 500 g, or greater than 1 kg.

Figure 1:
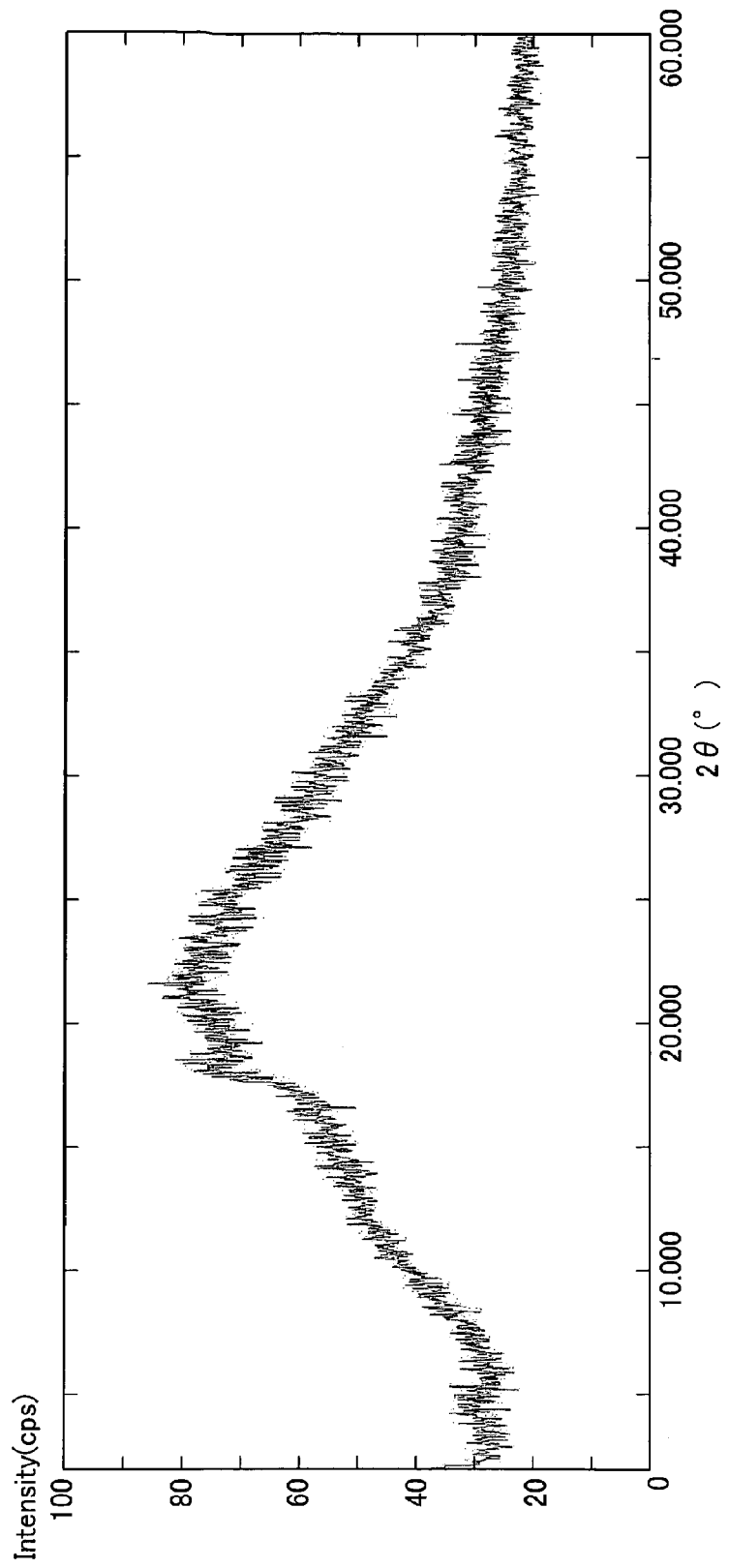
FIG. 1 shows the results of X-ray analysis of compound (1) obtained in Example 1 of the present invention.

EMBODIMENTS OF THE INVENTION
The method of the present invention will now be described in detail.
First, dipeptide compound (4) is produced by dehydrocondensation of L-phenylalanine amide and Boc-L-Lys(Cbz)-OH and then Boc deprotection of the product. Next, tripeptide compound (5) is produced by dehydrocondensa-
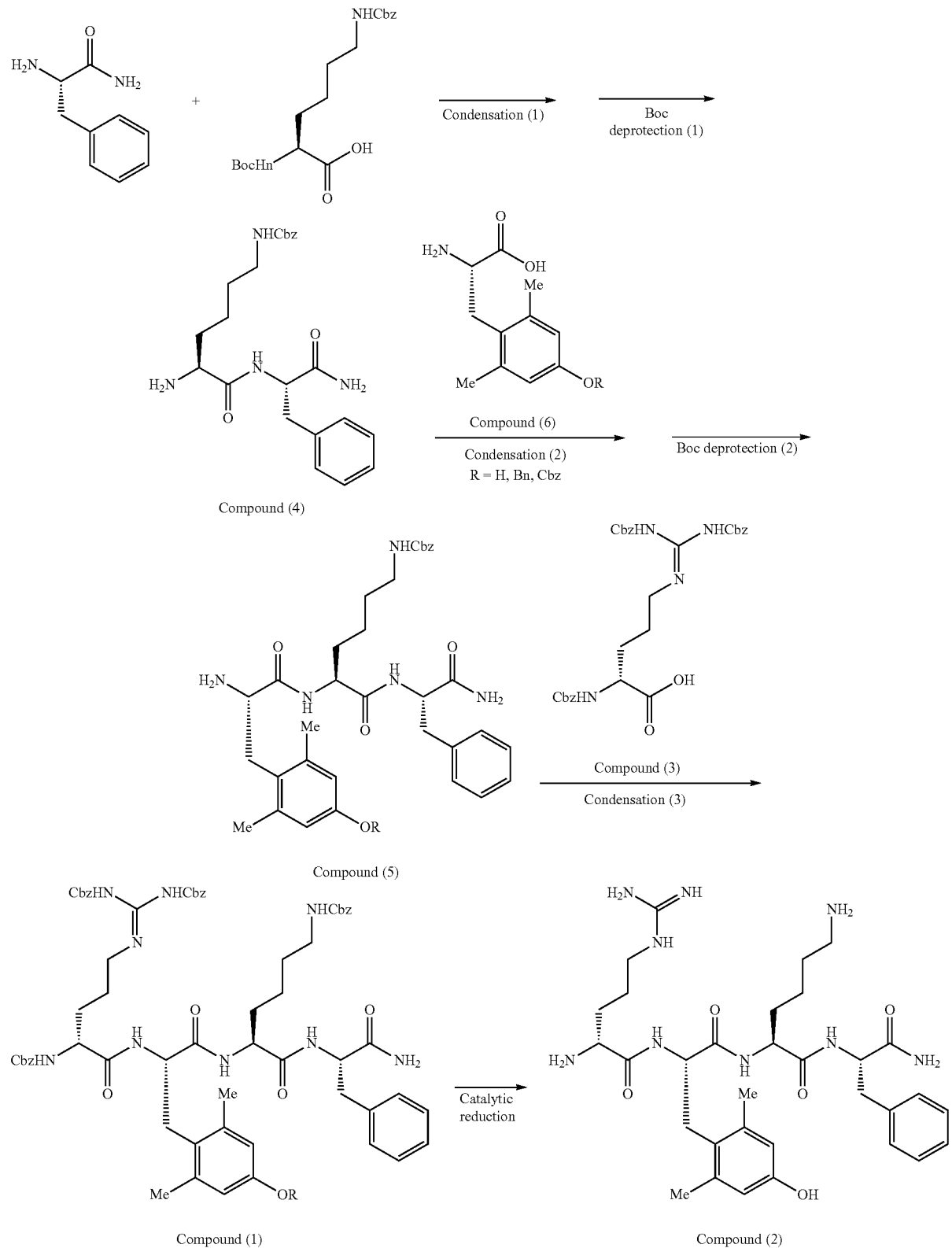

tion of dipeptide compound (4) and an N-Boc-L-2,6-dimethyltyrosine compound represented by the following formula (6)

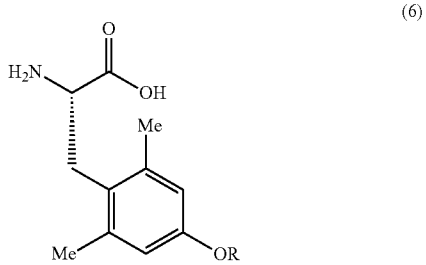

(6)

(where R is a hydrogen atom, benzyl group, or benzyloxycarbonyl group) and then Boc deprotection of the product. Next, tetrapeptide compound (1) is produced by dehydrocondensation of tripeptide compound (5) and Z-D-Arg(Z)2-OH represented by the following formula (3)

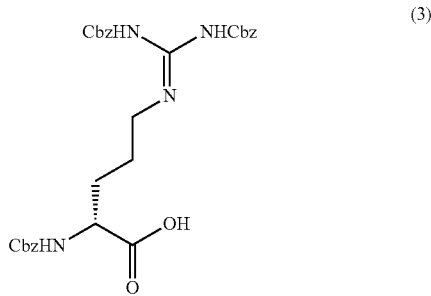 [SMILES: O=C(NC(=NCCC[C@@H](NC(=O)OCc1ccccc1)C(=O)O)NC(=O)OCc1ccccc1)OCc1ccccc1]

(3)

and the product is eventually catalytically reduced to produce compound (2), that is, SS-31.

Although there are no particular restrictions to the methods used for the dehydrocondensation and Boc deprotection, (continuous) liquid-phase synthesis is preferable for an industrial scale and can be performed while referring to the method described in International Publication WO 2007-099656, for instance. It should be noted that Boc is the abbreviation used for a tert-butoxycarbonyl group.

Examples of dehydrocondensation methods are the use of a carbodiimide compound in the presence of a hydroxylamine compound, or the use of a dehydrocondensation agent Examples of a hydroxylamine compound are 1-hydroxybenzotriazole (HOBt), 1-hydroxy-7-azabenzotriazole (HOAt), 3-hydroxy-4-oxo-3,4-dihydro-1,2,3-benzotriazine (HOOBt), N-hydroxysuccinimide (HONSu), ethyl 2-oximecyanoglyoxylate, N-hydroxyphthalimide, and N-hydroxypiperidine. 1-Hydroxybenzotriazole (HOBt), 1-hydroxy-7-azabenzotriazole (HOAt), and ethyl 2-oximecyanoglyoxylate are preferred. The maximum amount of hydroxylamine compound used is preferably 5 equivalents or less, further preferably 2 equivalents or less, in terms of the N-protected amino acid to be condensed. The minimum amount is preferably 0.1 equivalent or greater, further preferably 0.5 equivalent or greater.

Examples of the carbodiimide compound are dicyclohexylcarbodiimide (DCC) and 1-(3-dimethylaminopropyl)-3-ethylcarbodiimide hydrochloride (EDC). 1-(3-dimethylaminopropyl)-3-ethyl carbodiimide hydrochloride (EDC) is preferred. The maximum amount of carbodiimide compound used is preferably 5 equivalents or less, further preferably 2 equivalents or less, in terms of the N-protected amino acid to be condensed. The minimum amount is preferably 0.1 equivalent or greater, further preferably 0.5 equivalent or greater.

Examples of the dehydrocondensation agent are 1H-benzotriazol-1-yloxy-tris-dimethylaminophosphonium hexafluorophosphate (BOP), 1H-benzotriazol-1-yloxy-tris-pyrrolidinophosphonium hexafluorophosphate (PyBOP), O-benzotriazol-1-yl)-N,N,N',N'-tetramethyluronium hexafluorophosphate (HBTU), O-(7-azabenzotriazol-1-1-yl)-N,N,N',N'-tetramethyluronium hexafluorophosphate (HATU), O-(benzotriazol-1-yl)-N,N,N',N'-tetramethyluronium tetrafluoroborate (TBTU), O-[(ethoxycarbonyl)cyanomethylamino]-N,N,N',N'-tetramethyluronium hexafluorophosphate (HOTU), (1-cyano-2-ethoxy-2-oxoethylideneaminoxy)dimethylamino-morpholinocarbenium hexafluorophosphate (COMU), and 4-(4,6-dimethoxy-1,3,5-triazin-2-yl)-4-methyl morpholinium chloride (DMT-MM). O-benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), and (1-cyano-2-ethoxy-2-oxoethylidene aminoxy)dimethylamino morpholinocarbenium hexafluorophosphate (COMU) are preferred, and O-benzotriazol-1-yl)-N,N,N',N'-tetramethyluronium hexafluorophosphate (HBTU) is further preferred. The maximum amount of dehydrocondensation agent used is preferably 5 equivalents or less, further preferably 2 equivalents or less, in terms of N-protected amino acid to be condensed. The minimum amount used is preferably 0.1 molar equivalent or greater, further preferably 0.5 equivalent or greater.

It is possible to further add a base to the dehydrocondensation. The preferred base is a tertiary amine, and specific examples are triethylamine, pyridine, diisopropylethylamine, N-methylmorpholine, 2,6-dimethylpyridine, and 2,4,6-trimethylpyridine. Triethylamine, diisopropylethylamine, and 2,4,6-trimethylpyridine are preferred, and diisopropylethylamine is further preferred. The maximum amount of base used is preferably 5 equivalents or less, further preferably 2 equivalents or less, in terms of N-protected amino acid to be condensed. The minimum amount used is preferably 0.1 equivalent or greater, further preferably 0.5 equivalent or greater.

Examples of the reaction solvent used in dehydrocondensation are water; aliphatic hydrocarbon solvents such as hexane and heptane; halogen solvents such as dichloromethane, 1,2-dichloroethane, chloroform, and chlorobenzene; ether solvents such as tetrahydrofuran, 2-methyl tetrahydrofuran, 1,4-dioxane, tert-butyl methyl ether, and cyclopentyl methyl ether; ester solvents such as ethyl acetate, isopropyl acetate, and methyl propionate; nitrile solvents such as acetonitrile, propionitrile, and benzonitrile; ketone solvents such as acetone, methyl ethyl ketone, and acetophenone; and aprotic polar solvents such as N,N-dimethylformamide, N,N-dimethyl acetamide, N,N-diethylformamide, N,N-dipropylformamide, dibutyl formamide, dimethyl sulfoxide, N-methyl pyrrolidone, and 1,3-dimethyl propylene urea. Preferred solvents are halogen solvents such as dichloromethane, 1,2-dichloroethane, chloroform, and chlorobenzene; ether solvents, such as tetrahydrofuran, 2-methyl tetrahydrofuran, 1,4-dioxane, tert-butyl methyl ether, and cyclopentylmethyl ether; and aprotic polar solvents such as N,N-dimethylformamide, N,N-dimethyl acetamide, N,N-diethyl formamide, N,N-dipropyl formamide, N,N-dibuytl formamide, dimethylsulfoxide, N-methylpyrrolidone, and 1,3-dimethylpropylene urea. Dichloromethane, chlorobenzene, tetrahydrofuran, 2-methyltetrahydrofurane, N,N-dimethylformamide, and N,N-dimethyl acetamide are further preferred. These solvents can be used alone, or a mixture of two or more solvents can be used. There are no particular restrictions to the mixture ratio when these solvents are mixed. Using too much solvent is undesirable in terms of cost and post-treatment. The maximum amount is preferably 50-times by weight or less, further preferably 20-times by weight or less, in terms of the N-protected amino acid to be condensed. The minimum amount is preferably 1-time by weight or greater, further preferably 3-times by weight or greater.

The reaction temperature of dehydrocondensation is preferably the boiling point of the reaction solvent used or lower, further preferably 50° C. or lower, further preferably 30° C. or lower, particularly preferably 0 to 30° C.

With regard to the amount of N-protected amino acid used in dehydrocondensation, the amount of L-phenylalanine amide in the first condensation reaction is preferably 5 equivalents or less, further preferably 3 equivalents or less, particularly preferably 1 to 2 equivalents, in terms of the Boc-L-Lys(Cbz)-OH. The amount of N-Boc-L-2,6-dimethyl tyrosine derivative (compound (6)) used in the second condensation reaction is preferably 5 equivalents or less, further preferably 3 equivalents or less, particularly preferably 1 to 2 equivalents, in terms of compound 4. The amount of Z-D-Arg (Z)2-OH (compound (3)) used in the third condensation reaction is preferably 5 equivalents or less, further preferably 3 equivalents or less, particularly preferably 1 to 2 equivalents, in terms of compound (5).

There are no particular restrictions to the order of addition of the reagents. The carbodiimide compound can be added to a mixture formed from N-protected amino acid, peptide, reaction solvent, and hydroxylamine compound, or the dehydrocondensation agent can be added to a mixture formed from the N-protected amino acid, peptide, and reaction solvent.

Post-treatment can be performed by extraction after adding to the reaction solution water; an aqueous acid solution such as potassium hydrogen sulfate, sodium hydrogen sulfate, aqueous hydrochloric acid solution, aqueous sulfuric acid solution, aqueous phosphoric acid solution, aqueous acetic acid solution, or aqueous nitric acid solution; or an aqueous alkali solution such as aqueous sodium carbonate solution, aqueous potassium carbonate solution, aqueous sodium hydrogen carbonate solution, or aqueous sodium hydroxide solution, and when necessary, a solvent such as ethyl acetate, dichloromethane, chlorobenzene, tetrahydrofuran, 2-methyl tetrahydrofuran, or dibutyl formamide. The extract can be further rinsed with an aqueous acidic solution or aqueous alkali solution such as described above and then the hydroxylamine compound or condensation agent can be removed. The desired product is obtained from the resulting extract by performing heating under reduced pressure—and the like in order to distill of the reaction solvent and extraction solvent Although the product obtained in this way has sufficient purity such that it can be used in subsequent steps, it is also possible to improve purity further by a conventional purification step such as crystallization or column chromatography.

The Boc deprotection will now be described. Boc groups are protector groups of amino groups that can be deprotected under relatively weak acidity, and can react with acidic compounds for deprotection. Examples of the acidic groups are hydrogen halides such as hydrogen fluoride, hydrogen chloride, and hydrogen bromide; mineral acids such as sulfuric acid, nitric acid, and phosphoric acid; carboxylic acids such as formic acid, acetic acid, oxalic acid, and trifluoroacetic acid; and sulfonic acids such as methanesulfonic acid, p-toluenesulfonic acid, p-nitrosulfonic acid, and trifluoromethanesulfonic acid. Preferred acidic compounds are sulfonic acids such as methanesulfonic acid, p-toluenesulfonic acid, p-nitrosulfonic acid, and trifluoromethanesulfonic acid, and methanesulfonic acid is further preferred. These can also be used as mixtures. The maximum amount of acidic compound used is preferably 20 equivalents or less, further preferably 10 equivalents or less, in terms of N-Boc protected peptide. The minimum amount is preferably 0.1 equivalent or greater, further preferably 0.5 equivalent or greater.

Although depending on the type of acid used, a reaction solvent is not particularly necessary for Boc deprotection, it will improve the liquid state and accelerate the reaction, and a reaction solvent can also be added in order to prevent side reactions. Examples of reaction solvents are water; alcoholic solvents such as methanol, ethanol, isopropanol, n-butanol, and ethylene glycol; aliphatic hydrocarbon solvents such as hexane and heptane; halogen solvents such as dichloromethane, 1,2-dichloroethane, chloroform, and chlorobenzene; ether solvents such as tetrahydrofuran, 2-methyl tetrahydrofuran, 1,4-dioxane, tert-butyl methyl ether, and cyclopentyl methyl ether; ester solvents such as ethyl acetate, isopropyl acetate, and methyl propionate; nitrile solvents, such as acetonitrile, propionitrile, and benzonitrile; ketone solvents such as acetone, methyl ethyl ketone, and acetophenone; and aprotic polar solvents such as N,N-dimethylformamide, N,N-dimethyl acetamide, N,N-diethyl formamide, N,N-dipropyl formamide, N,N-dibutyl formamide, dimethyl sulfoxide, N-methyl pyrrolidone, and 1,3-dimethyl propylene urea. Preferred solvents are halogen solvents such as dichloromethane, 1,2-dichloroethane, chloroform, and chlorobenzene; ether solvents such as tetrahydrofuran, 2-methyl tetrahydrofuran, 1,4-dioxane, tert-butyl methyl ether, and cyclopentyl methyl ether; ester solvents such as ethyl acetate, isopropyl acetate, and methyl propionate; and aprotic polar-solvents-such as N,N-dimethylformamide, N,N-dimethyl acetamide, N,N-diethyl formamide, N,N-dipropyl formamide, N,N-dibutylformamide, dimethyl sulfoxide, N-methyl pyrrolidone, and 1,3-dimethyl propylene urea. Dichloromethane, chlorobenzene, tetrahydrofuran, 2-methyl tetrahydrofuran, ethyl acetate, N,N-dimethylformamide, and N,N-dimethyl acetamide are further preferred. These solvents can be used alone, or a mixture of two or more can be used. There are no particular restrictions to the mixture ratio when the solvents are mixed. Using too much solvent is undesirable in terms of cost and post-treatment and therefore, the maximum amount is preferably 50-times by weight or less, more preferably 20-times by weight or less, in terms of N-Boc protected peptide. The minimum amount is preferably 1-time by weight or greater, further preferably 3-times by weight or greater.

The reaction temperature for Boc deprotection is the boiling temperature of the reaction solvent used or lower, preferably 50° C. or lower, further preferably 40° C. or lower, particularly preferably 0 to 40° C.

There are no particular restrictions to the order of addition of the reagents, but an acidic compound should be added to a reaction mixture formed from N-Boc protected peptide and reaction solvent.

Post-treatment can be performed by extraction after adding to the reaction solution an aqueous sodium carbonate solution, aqueous potassium carbonate solution, aqueous sodium bicarbonate solution, or aqueous sodium hydroxide solution and when necessary, adding a solvent such as ethyl acetate, dichloromethane, chlorobenzene, tetrahydrofuran, 2-methyl tetrahydrofuran, or dibutyl formamide. The desired product is obtained from the resulting extract by heating under reduced pressure in order to distill off the reaction solvent and extraction solvent. The resulting product has sufficient purity to be used in subsequent steps, but it is possible to further improve purity by a conventional purification means such as crystallization or column chromatography.

Moreover, the tetrapeptide compound that is produced by dehydrocondensation of compound (3) and compound (5) and is represented by the following formula (1)

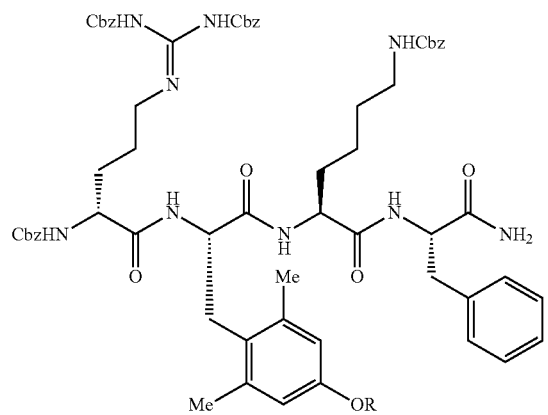

(1)

can be further purified by precipitation as a solid from an aprotic polar solvent. Here, the R is a hydrogen atom, benzyl group, or benzyloxycarbonyl group. A hydrogen atom or benzyl group is preferred, and a hydrogen atom is further preferred.

Examples of the aprotic polar solvent are tetrahydrofuran, N,N-dimethylformamide, N,N-dimethyl acetamide, N,N-diethyl formamide, N,N-dipropyl formamide, N,N-dibutyl formamide, dimethyl sulfoxide, N-methyl pyrrolidone, and 1,3-dimethylpropylene urea. Tetrahydrofuran, N,N-dimethylformamide, N,N-dimethyl acetamide, and dimethyl sulfoxide are preferred, and N,N-dimethylformamide is further preferred. These aprotic polar solvents can be used alone, or a mixture of two or more solvents can be used. There is no particular restriction to the mixture ratio thereof when these solvents are mixed. Using too much solvent is undesirable in terms of cost and post-treatment and therefore, the maximum amount is preferably 100-times by weight or less, further preferably 50-times by weight or less, in terms of above-mentioned compound (1). The minimum amount is preferably 1-time by weight or greater, further preferably 3-times by weight or greater.

Moreover, an auxiliary solvent can further be added in order to improve the yield, improve the purity, guarantee fluidity, and the like. The auxiliary solvent can be water; an alcohol solvent such as methanol, ethanol, isopropanol, n-butanol, or ethylene glycol; an aliphatic hydrocarbon solvent such as hexane or heptane; a halogen solvent such as dichloromethane, 1,2-dichloroethane, chloroform, or chlorobenzene; an ether solvent such as 2-methyl tetrahydrofuran, 1,4-dioxane, tert-butyl methyl ether, or cyclopentyl methyl ether; an ester solvent such as ethyl acetate, isopropyl acetate, or methyl propionate; a nitrile solvent such as acetonitrile, propionitrile, or benzonitrile; a ketone solvent such as acetone, methyl ethyl ketone, or acetophenone; or an aprotic polar solvent such as N,N-dimethylformamide, N,N-dimethyl acetamide, N,N-diethyl formamide, N,N-dipropyl formamide, N,N-dibutyl formamide, dimethyl sulfoxide, N-methyl pyrrolidone, and 1,3-dimethyl propylene urea. Water, methanol; ethanol, isopropanol, dichloromethane, tetrahydrofuran, 2-methyl tetrahydrofuran, ethyl acetate, acetonitrile, and acetone are preferred, and water, acetonitrile, and acetone are further preferred. These auxiliary solvents can be used alone, or a mixture of two or more solvents can be used. There are no particular restrictions to the mixture ratio thereof when the solvents are mixed.

Using too much solvent is undesirable in terms of cost and post-treatment and therefore, the maximum amount is preferably 100-times by weight or less, further preferably 50-times by weight or less, in terms of above-mentioned compound (1). The minimum amount is preferably 1-time by weight or greater, further preferably 3-times by weight or greater.

Although there are no particular restrictions to the method for precipitating compound (1) as a solid, the following methods are examples:

(a) Method whereby compound (1) is dissolved in the aprotic polar solvent, the product is cooled, and the solid is precipitated.

(b) Method whereby compound (1) is dissolved in the aprotic polar solvent, and then the solid is precipitated by concentration.

(c) Method whereby compound (1) is dissolved in the aprotic polar solvent, and then the solid is precipitated by further adding an auxiliary solvent.

(d) Method whereby compound (1) is dissolved in the aprotic polar solvent, and then the solid is precipitated by further concentration and substitution in auxiliary solvent. Moreover, the solid can be precipitated by using any combination of methods (a) through (d). Furthermore, solid that serves as the seed can be added when the solid is-precipitated.

There are no particular restrictions to the temperature of methods (a) through (d) for precipitating the solid. Preferably, temperature is set in accordance with the desired amount of precipitation and solid quality and at less than the temperature at which compound (1) will dissolve in the solvents that are used.

Compound (1) precipitated by solid precipitation methods (a) through (d) can be separated and recovered by filtration under reduced pressure, filtration under increased pressure, or centrifugation. Moreover, when chemical purity of the solid is reduced by residual mother liquor contained in the recovered solvent, quality can be improved by further rinsing with solvent as necessary.

Although there are no particular restrictions to the solid drying method, it is desirable to conduct drying under reduced pressure (vacuum drying) at approximately 60° C. or a lower in order to avoid pyrolysis and melting.

Moreover, when chemical purity is not sufficiently improved, it is possible to repeat the method of solid precipitation according to any of (a) through (d) or to rinse compound (1) with a solvent, but the solid should be reprecipitated by a method in accordance with any of the above-mentioned methods (a) through (d). The solid compound (1) obtained in this way often is obtained as an amorphous product, but it can be amorphous, crystals, semicrystals, or a mixture thereof.

It should be noted that compound (1) obtained by the present invention is a novel compound not disclosed in any publications and is of course unknown in solid form.

Finally, when compound (1) is catalytically reduced, the peptide pharmaceutical drug (SS-31) represented by the following formula (2)

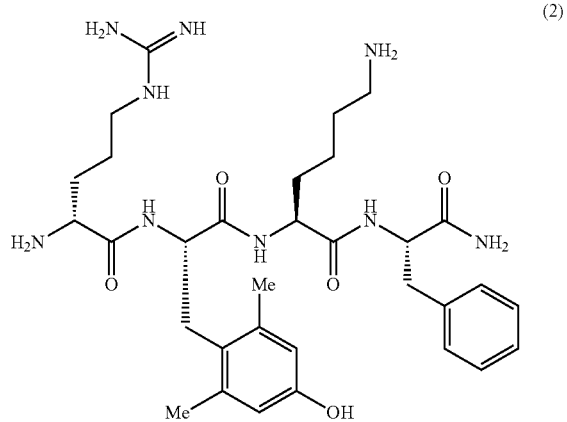 [SMILES: Cc1cc(O)cc(C)c1C[C@H](NC(=O)[C@H](N)CCCNC(=N)N)C(=O)N[C@@H](CCCCN)C(=O)N[C@@H](Cc1ccccc1)C(N)=O]

is obtained. Here, the amino groups of compound (2) are all protected by Cbz groups (benzyloxycarbonyl groups) and the phenol hydroxyl groups are either unprotected or protected by benzyl groups or Cbz groups. Therefore, it is possible to simultaneously remove all of the protective groups by one catalytic reduction. Moreover, the only by-products of catalytic reduction are toluene and carbon dioxide and these by-products can be removed by concentration under reduced pressure. Therefore, there is no reduction in chemical purity of the product.

The catalytic reduction should be hydrogenation in the presence of a palladium catalyst. Examples of palladium catalysts are palladium black, palladium-carbon, palladium hydroxide-carbon; palladium-alumina, palladium-silica gel, palladium-barium sulfate, and palladium-calcium carbonate. Palladium-carbon and palladium hydroxide-carbon are preferred. Palladium-carbon is further preferred. Using too much palladium catalyst is undesirable in terms of cost and post-treatment. Therefore, the maximum is 5-times by weight or less, further preferably 1-time by weight or less, in terms of compound (2). The minimum is preferably 0.01-time by weigh for greater, further preferably 0.05-time by weight or greater.

The hydrogen can be normal-pressure hydrogen, but it is also possible to pressurize the hydrogen in order to accelerate the reaction. The maximum hydrogen pressure is preferably 100 atmospheres or less, further preferably 10 atmospheres or less.

Examples of solvents that can be used for this step are water; alcoholic solvents such as methanol, ethanol, isopropanol, n-butanol, and ethylene glycol; ether solvents such as tetrahydrofuran, 2-methyltetrahydrofuran, 1,4-dioxane, tert-butyl methyl ether, and cyclopentyl methyl ether; ester solvents such as ethyl acetate, isopropyl acetate, and methyl propionate; and aprotic polar solvents, such as N,N-dimethylformamide, N,N-dimethyl acetamide, N,N-diethyl formamide, N,N-dipropyl formamide, dibutyl formamide, dimethyl sulfoxide, N-methyl pyrrolidone, and 1,3-dimethylpropylene urea. Water; alcoholic solvents such as methanol, ethanol, isopropanol, n-butanol, and ethylene glycol; and ether solvents such as tetrahydrofuran, 2-methyl tetrahydrofuran, 1,4-dioxane, tert-butyl methyl ether, and cyclopentyl methyl ether are preferred, and methanol, ethanol, and tetrahydrofuran are further preferred. These solvents can be used alone, or a mixture of two or more solvents can be used. There are no particular restrictions to the mixture ratio of the solvents when they are mixed. Using too much solvent is undesirable in terms of cost and post-treatment. Therefore, the maximum is preferably 100-times by weight or less, further preferably 50-times by weight or less, in terms of compound (2). The minimum is preferably one-time by weight or greater, further preferably 3-times by weight or greater.

Moreover, an acid can be added in order to accelerate the reaction. Examples of this acid are hydrochloric acid, hydrobromic acid, sulfuric acid, phosphoric acid, acetic acid, and citric acid. When an acid is added, the maximum amount added is preferably 10-times by weight or less, further preferably 5-times by weight or less, in terms of compound (2). The minimum amount is preferably 0.1-times by weight or greater, further preferably 1-time by weight or greater.

There are no particular restrictions to the order in which the reagents are added, but hydrogen should be added to a mixture comprising compound (2), palladium catalyst, and reaction solvent.

The only products of the reaction other than the desired product are toluene and carbon dioxide. Therefore, the desired product is obtained by post-treatment in the form of simply filtering the palladium catalyst from the reaction solution and distilling the reaction solvent and toluene off under reduced pressure. Although the desired product obtained in this way already has sufficient purity, purity can be further increased by conventional purification methods such as crystallization and column chromatography. Moreover, the product can be crystallized as a salt of an acceptable acid.

EXAMPLES

Although the present invention will now be described in further detail using examples, the present invention is in no way restricted to these examples.

The yield and production ratio of each compound produced in the examples was analyzed under the following conditions using high-performance liquid chromatography.

(High-performance Liquid Chromatography Analytical Conditions)
Column: Zorbax Eclipse Plus C18, 50×4.6 mm; 1.8 µm
Mobile phase A: aqueous 0.1 wt % phosphoric acid solution, mobile phase B: acetonitrile
Current speed: 1.0 mL/min
Gradient Conditions
0.00 minute Mobile phase A:mobile phase B=90:10
15.00 minutes Mobile phase A:mobile phase B=10:90
20.00 minutes Mobile phase A:mobile phase B=10:90
20.01 minutes Mobile phase A:mobile phase B=90:10
25.00 minutes STOP
Column temperature: 40°
Detection wavelength: 210 nm Example 1

Method for Producing Compound (1)
Phenylalanine amide (330 mg, 2.01 mmol), N6-Cbz-N2-Boc-L-lysine (931 mg, 2.45 mmol), HOBt (415 mg, 3.07 mmol), and EDC (583 mg, 3.04 mmol) were stirred for 1.5 hours in methylene chloride (10 mL). An aqueous 10 wt % sodium carbonate solution (5 g) was added to the reaction solution. The solution was heated to 37° C. and separated. The organic layer was rinsed with water (5 g).
Methanesulfonic acid (763 mg, 7.94 mmol) was added and stirred for four hours. An aqueous 10 wt % sodium carbonate solution (9 g) was added to the reaction solution. Then the dichloromethane was distilled off under reduced pressure and the solid precipitate was filtered to obtain 844 mg of compound (4). N-Boc-L-2,6-dimethyl tyrosine (311 mg, 1.00 mmol), HOBt (162 mg, 1.20 mmol), EDC (230 mg, 1.20 mmol), tetrahydrofuran (5 mL), and 2-methyl tetrahydrofuran (5 mL) were added to resulting compound (4) (431 mg, 1.00 mmol) and stirred for four hours. 5 wt % potassium hydrogen sulfate (1.25 g) was added to the reaction solution and stirred for three hours, and then the solution was fractionated. The organic layer was rinsed with 5 wt % sodium carbonate (1.25 g) and water (1.25 g) and concentrated. Tetrahydrofuran (5 mL) and methanesulfonic acid (765 mg, 7.96 mmol) were added to the concentrate and stirred for 14 hours. Then triethylamine (855 mg, 8.45 mmol), Z-D-Arg(Z)2-OH.0.1 hydrate (579 mg, 1.00 mmol), HOBt (163 mg, 1.21 mmol), and EDC (231 mg, 1.21 mmol) were added and stirred for 2.5 hours. An aqueous 5 wt % sodium carbonate solution (10 g) was added to the reaction solution. The solid precipitate was filtered and then dried under reduced pressure at 50° C. to obtain compound (1) (1.13 g) as a white solid. N,N-dimethylformamide (1.40 g) was added to the resulting compound (1) (123 mg) and dissolved. Water (5 mL) was added and the solid precipitate was filtered. The filtration product was washed with water (2 mL) and ethanol (2 mL) and dried under reduced pressure to obtain compound (1) (97.7 mg). The resulting compound (1) had a purity of 93 area % and the high-performance liquid chromatography retention time was 14.8 minutes. According to the results of X-ray powder analysis of compound (1) shown in FIG. 1 (X-ray powder analyzer: Rigaku MiniFlex-II; determination conditions: $CuK_{\alpha 1}$ rays, tube voltage 30 kV, tube current 15 mA), Compound (1) was obtained in the form of an amorphous solid.

Compound (1)

$^1$HNMR (DMSO-$d_6$) δ 8.85 (s, 1H), 8.10 (d, J=8.6 Hz, 1H), 7.88 (d, J=7.4 Hz, 1H), 7.74 (d, J=8.0 Hz, 1H), 7.14-7.40 (m, 30H), 6.86 (s, 1H), 6.30 (s, 2H), 5.23 (s, 2H), 5.03 (dd, J=16.3, 12.3 Hz, 2H), 4.98 (s, 2H), 4.95 (dd, J=26.5, 12.5 Hz, 2H), 4.50 (dd, J=14.9, 8.6 Hz, 1H), 4.39 (td, J=8.3, 5.3 Hz, 1H), 4.13 (dd, J=13.7, 8.0 Hz, 1H), 3.95 (td, J=8.0, 4.6 Hz, 1H), 3.74-3.84 (m, 2H), 3.01 (dd, J=13.5, 4.9 Hz, 1H), 2.87-2.95 (m, 3H), 2.82 (dd, J=13.7, 8.6 Hz, 1H), 2.67 (dd, J=14.3, 9.2 Hz, 1H), 2.12 (s, 6H), 1.10-1.69 (m, 10H)

Example 2

Method for Producing Compound (2)

Palladium carbon (N. E. Chemcat Corporation A-10D, 9.2 mg) and MeOH (3 mL) were added to compound (1)(94.5 mg) obtained as in Example 1 and hydrogen substitution was performed. The reaction solution was stirred for two hours at 50° C. Then the palladium carbon was filtered and the filtrate was concentrated and dried to obtain compound (2) (57 mg). The resulting compound (2) was 94 area %.

Example 3

Method for Producing Compound (2)

The compound in the title was obtained at a yield of 100% by the same procedure as in Example 2, with the exception that tetrahydrofuran (4 g) and water (1 g) were used in place of methanol and acetic acid (19 mg) was added. The purity of the resulting compound (2) was 98 area %.

Example 4

Method for Purifying Compound (1)

Tetrahydrofuran (5.22 g) and water (3.96 g) were added to compound (1) (89 area %, 316 mg) obtained as in Example 1 and heated to 50° C. After stirring for one hour, the product was cooled to room temperature. The solid was filtered, rinsed twice with a mixture of tetrahydrofuran/water=1 mL/1 mL, and dried under reduced pressure at 50° C. to obtain compound (1) (305 mg). Purity of the resulting compound (1) was 97 area %.

Example 5

Method for Purifying Compound (1)

Dimethylsulfoxide (1 g) was added to compound (1) (89 area %, 100 mg) obtained as in Example 1 and heated to 50° C. Then acetonitrile (5 g) was added. After stirring for an hour, the product was cooled to room temperature. The solid precipitate was filtered, rinsed twice with acetonitrile (1 mL) and dried under reduced pressure at 50° C. to obtain compound (1) (76 mg). The purity of the resulting compound (1) was 94 area %.

Example 6

Method for Purifying Compound (1)

Compound (1) (41 mg) was obtained by the same procedure as in Example 5, with the exception that N,N-dimethylformamide was used in place of dimethylsulfoxide and acetone was used in place of acetonitrile. Purity of the resulting compound (1) was 95 area %.

Example 7

Method for Producing Compound (7)

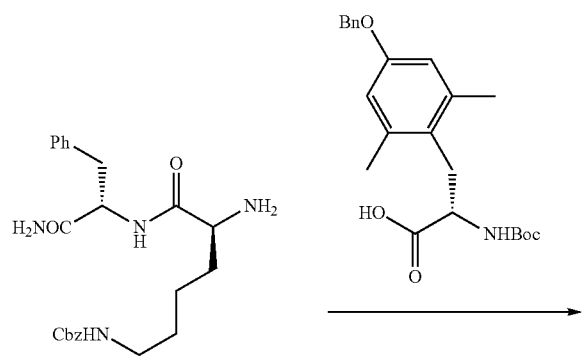

Compound (4)

-continued

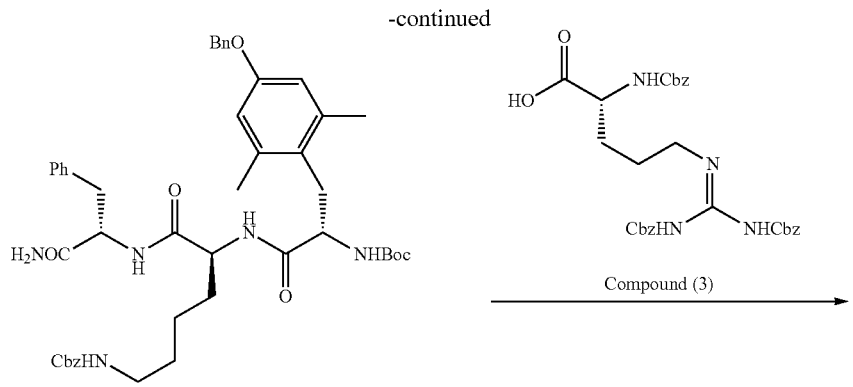

Compound (3)

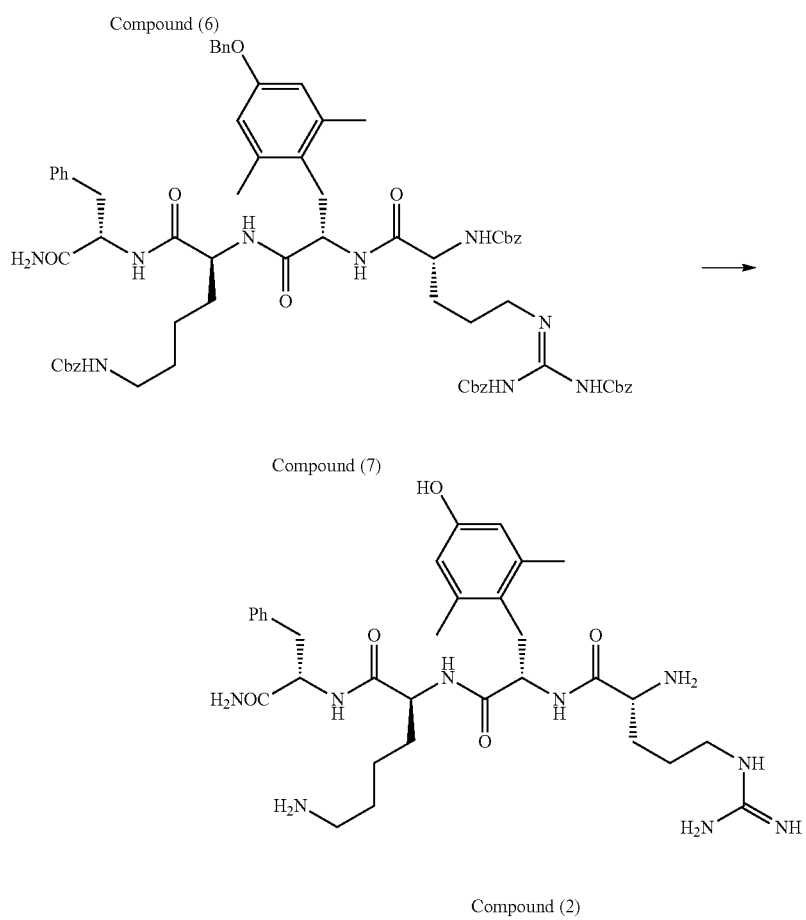

Compound (4) (215 mg, 0.50 mmol), O-Bn-N-Boc-L-2,6-dimethyltyrosine (purity 91.4 wt %, 240 mg, 0.55 mmol), EDC (115 mg, 0.60 mmol), and HOBt (81 mg, 0.60 mmol) were stirred for 50 minutes in a mixed solvent of tetrahydrofuran (2.5 mL) and 2-methyl tetrahydrofuran (2.5 mL). Then tetrahydrofuran (2.5 mL) and 2-methyl tetrahydrofuran (2.5 mL) were added to the reaction solution and stirred for 18 hours. Aqueous 5 wt % potassium hydrogen sulfate solution (2.5 g) was added to the reaction solution and stirred for 45 minutes. Aqueous 5 wt % sodium carbonate solution (2.5 g) was added to the reaction solution. The reaction solution was stirred for five minutes and then separated. The solid precipitate was filtered. The filtration product was rinsed with water (2 mL) and tetrahydrofuran (2 mL) and then dried under reduced pressure at 50° C. to obtain compound (A) (190 mg) as a white solid.

Methanesulfonic acid (107 mg, 1.65 mmol) and tetrahydrofuran (5 mL) were added to above-mentioned compound (6) (178 mg) and stirred for 2.5 hours. The product was heated to 50° C. and stirred for another 20 hours. Tetrahydrofuran (5 mL) was added to the reaction solution and stirred for 2.5 hours under reflux conditions. Methanesulfonic acid (27 mg, 0.28 mmol) was added to the reaction solution and stirred for 3.5 hours under reflux conditions. After cooling to room temperature, triethylamine (210 mg, 2.07 mmol) was added to the reaction solution and stirred for 2 hours. Z-D-Arg(Z)2-OH·0.1 hydrate (288 mg, 0.50 mmol), EDC (115 mg, 0.60 mmol), and HOBt (81 mg, 0.60 mmol) were added to this reaction solution and stirred for 20.5 hours. Then aqueous 5 wt % potassium hydrogen sulfate solution (2.5 g) was added to the reaction solution and stirred for 30 minutes. Aqueous 5 wt % sodium carbonate solution (2.5 g) was added to the reaction solution and stirred for 1.5 hours. The solid precipitate was filtered. The filtration product was rinsed with water (2 mL) and tetrahydrofuran (2 mL) and then dried under reduced pressure at 50° C. to obtain compound (7) (286 mg) as a white solid. Purity of the resulting compound (7) was 71 area %. The high-performance liquid chromatography retention time of compound (7) was 17.0 minutes.

Example 8

Method for Producing Compound (2)

Palladium carbon (N. E. Chemcat Corporation A-10D, 22 mg) and methanol were added to compound (7) (110 mg) obtained as in Example 3 and hydrogen substitution was performed. The reaction solution was stirred for 21 hours under refluxing. Methanol (2.2 g) was added to the reaction solution and hydrogen substitution was performed. The reaction solution was stirred for 2.5 hours under refluxing. The palladium carbon was filtered and the filtrate was concentrated and dried under reduced pressure at 50° C. to obtain compound (2) (52.1 mg) as a pale orange solid. The purity of the resulting compound (2) was 72 area %.

Example 9

Method for Producing Compound (1)

N6-Cbz-N2-Boc-L-lysine (7.38 g, 19.4 mmol), L-phenylalanine amide hydrochloride (4.67 g, 23.3 mmol), HOBt monohydrate (3.56 g, 23.3 mmol), and THF (50.9 g) were cooled to 5° C. After triethylamine (2.36 g, 23.3 mmol) was added, an aqueous 50 wt % EDC solution (8.92 g, 23.3 mmol) was further added. The reaction solution was stirred for 7 hours and then an aqueous 5 wt % sodium carbonate solution (20.6 g) was added and the temperature of the mixture was raised to 25° C. The reaction solution was extracted with ethyl acetate (32.5 g) and the organic layer was rinsed with an aqueous 5 wt % sodium carbonate solution (20.6 g) twice. Ethyl acetate (391.2 g) was added to the organic layer and the organic phase was concentrated to 204 g of concentrate. Methanesulfonic acid (13.4 g, 0.139 mol) was added to the concentrate and the mixture was stirred for 4 hours at 25° C. The reaction solution was added to a mixture of an aqueous 5 wt % sodium carbonate solution (347.9 g) and MeOH (60.7 g). Then the reaction solution was concentrated to 359 g of concentrate and the solid precipitate was obtained by filtration. Thus obtained wet crystalline compound was washed with water (61 g) and dried under reduced pressure at 40° C. to obtain compound (4) (7.13 g, 16.7 mmol).

To the compound (4) (7.13 g, 16.7 mmol) obtained above, N-Boc-L-2,6-dimethyl tyrosine (5.69 g, 18.4 mmol), HOBt monohydrate (3.07 g, 20.0 mmol), and tetrahydrofuran (73.4 g) were added and then an aqueous 50 wt % EDC solution (7.69 g, 20.0 mmol) was added. After the reaction solution was stirred for 3 hours, an aqueous 5 wt % KHSO$_4$ solution (72.8 g) and ethyl acetate (70.6 g) were added to the reaction solution and the mixed solution was stirred for 12 hours, and then the solution was fractionated. The organic layer was washed at 40° C. with an aqueous 5 wt % sodium carbonate solution (85.0 g) four times followed by water (80.8 g). THF (890.7 g) was added to the organic layer and the organic phase was concentrated to obtain 271 g of concentrate. To the organic layer, methanesulfonic acid (14.2 g, 0.148 mol) was added and stirred for 12 hours at 40° C. To the reaction solution, an aqueous 12.5 wt % potassium carbonate solution (211 g) and DMF (57.1 g) were added and the solution was heated to 40° C. and fractionated. Water (148 g) was added to the organic layer and the mixture was stirred for 12 hours at 30° C. Further water (148 g) was added. The reaction solution was cooled to 0° C. and the solid precipitate was obtained by filtration. Thus obtained wet crystalline compound was washed with a mixture of THF (30 mL) and water (30 mL) and dried under reduced pressure at 30° C. to obtain compound (5) (8.75 g, 14.2 mmol).

Figure 2:
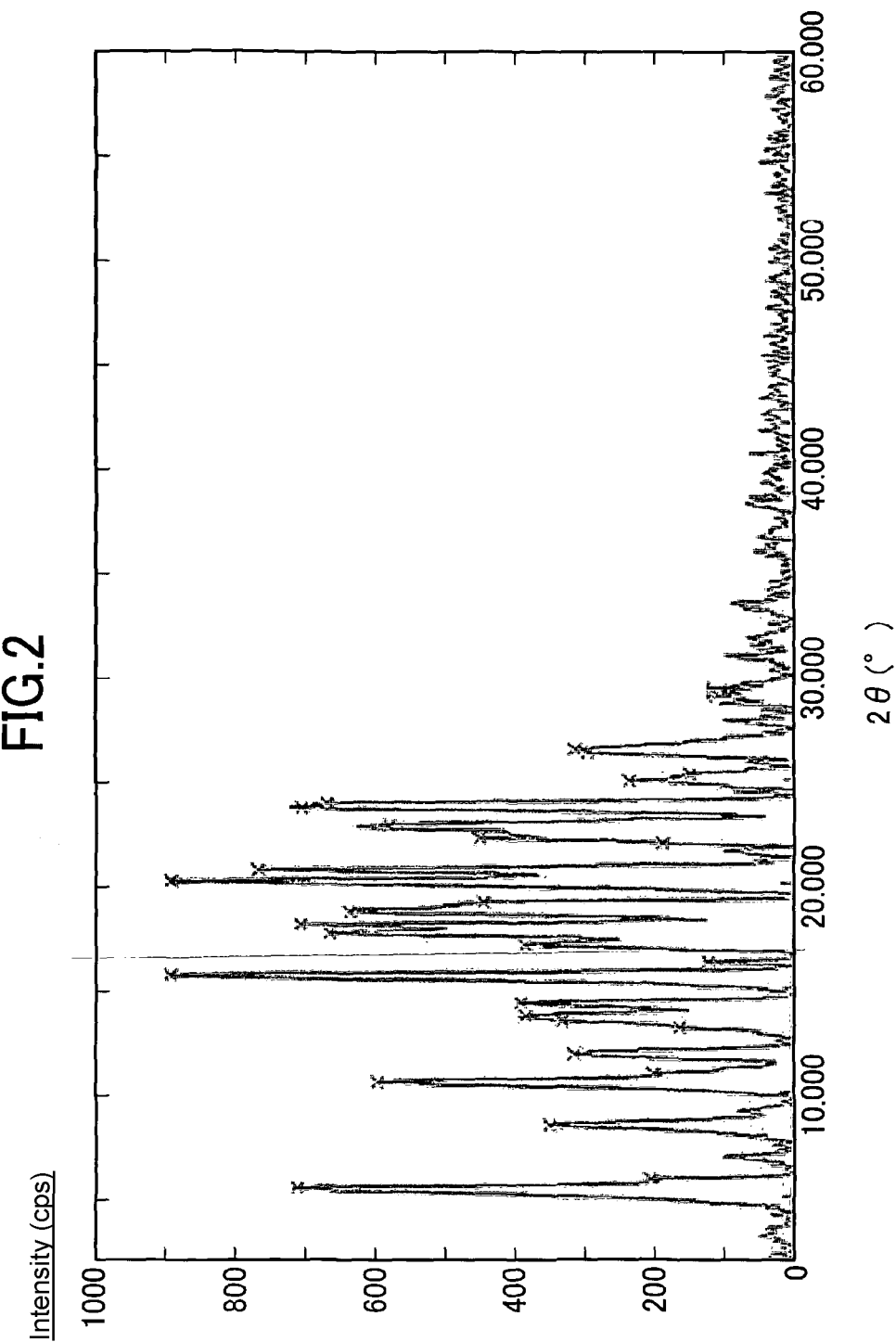
FIG. 2 shows the results of X-ray analysis of crystalline compound (1) obtained in Example 9 of the present invention.

Then Z-D-Arg(Z)2-OH (8.58 g, 14.9 mmol), THF (34.3 g), HOBt monohydrate (2.60 g, 17.0 mmol), DMF (87.6 g), and water (8.75 g) were added. Then an aqueous 50 wt % EDC solution (6.52 g, 17.0 mmol) was added at 0° C. and the mixture was stirred for 6 hours. The reaction solution was added to MeOH (271 g) and precipitated solid was obtained by filtration. Thus obtained wet crystalline was washed with MeOH (349 mL). Further DMF (108 g) was added to the wet crystalline and then it was concentrated under reduced pressure to obtain 130 g of concentrate. The concentrate was poured into MeOH (323 g). Precipitated solid was obtained by filtration. Thus obtained wet crystalline was washed with MeOH (240 mL) and dried under reduced pressure to obtain compound (1) (13.6 g, 11.6 mmol). The resulting compound (1) had a purity of 99 area %. FIG. 2 shows X-ray powder analysis of the resulting compound (1) (Rigaku MiniFlex-II; determination conditions: CuK$_{\alpha1}$ rays, tube voltage 30 kV, tube current 15 mA), Compound (1) was obtained in the form of an amorphous solid. According to the results, Compound (1) was obtained in the form of a crystalline solid.

Powder X-ray diffraction spectrum obtained using CuK$_{\alpha1}$ radiation of compound (1) at 2θ±0.1: 5.4°, 5.8°, 8.4°, 10.5°, 10.9°, 11.8°, 13.1°, 13.4°, 13.6°, 14.3°, 15.6°, 16.3°, 17.1°, 17.6°, 18.0°, 18.6°, 19.1°, 20.1°, 20.6°, 21.9°, 22.1°, 22.8°, 23.6°, 23.8°, 24.9°, 25.3°, 26.2°, 26.4°, 29.0°, 29.2°, and 29.4°

Example 10

Method for Producing Compound (2)

The same procedures as described in Example 3 excepting that no acetic acid is used, were repeated. Compound (2) was obtained in 96% yield. The resulting compound (2) had a purity of 99 area %.

The invention claimed is:

1. A tetrapeptide compound represented by the following formula (1)

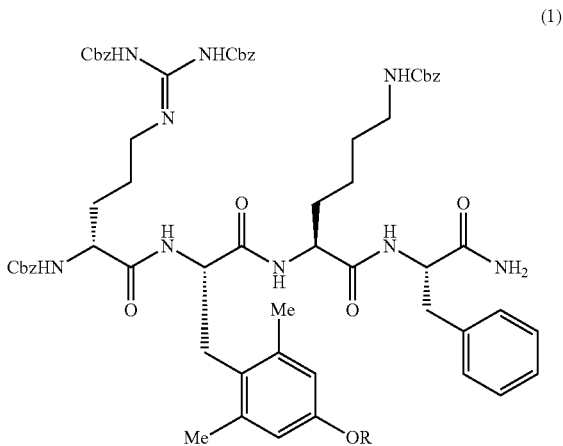

where R is a hydrogen atom, benzyl group, or benzyloxycarbonyl group.

2. The tetrapeptide compound according to claim 1, which is an intermediate for producing a peptide drug represented by the following formula (2)

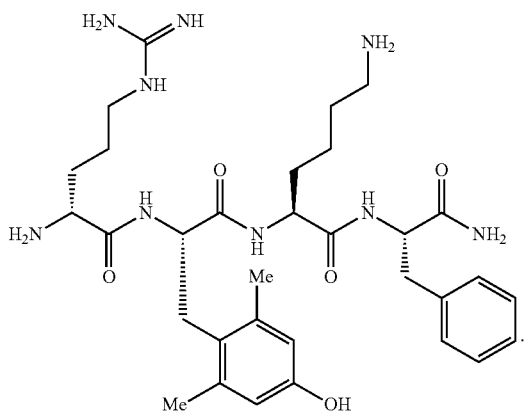

(2)

3. The tetrapeptide compound according to claim 1, where R is a hydrogen atom.

4. The tetrapeptide compound according to claim 1, where compound (1) is an amorphous solid.

5. The tetrapeptide compound according to claim 1, wherein the compound is in the form of a crystalline solid and exhibits one or more peaks at 2θ±0.1 selected from 5.4°, 10.5°, 15.6°, 17.6°, 18.0°, 18.6°, 20.1°, or 20.6° in a powder X-ray diffraction spectrum obtained using Cu-Kα radiation.

6. The tetrapeptide compound according to claim 1, wherein compound (1) is in a form of an amorphous solid or a crystalline solid.

7. A method for producing a peptide pharmaceutical, characterized in that the tetrapeptide compound represented by the following formula (1)

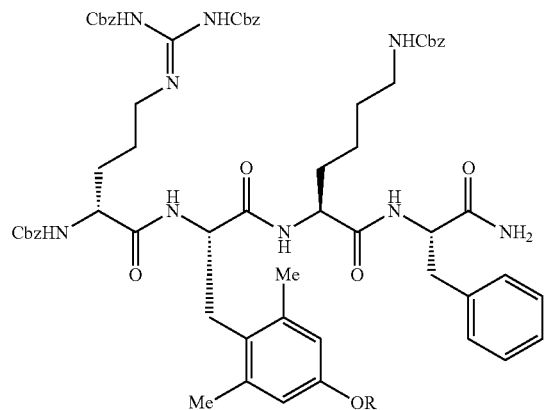

(1)

is catalytically reduced in the presence of a palladium catalyst to produce a peptide pharmaceutical represented by the following formula (2)

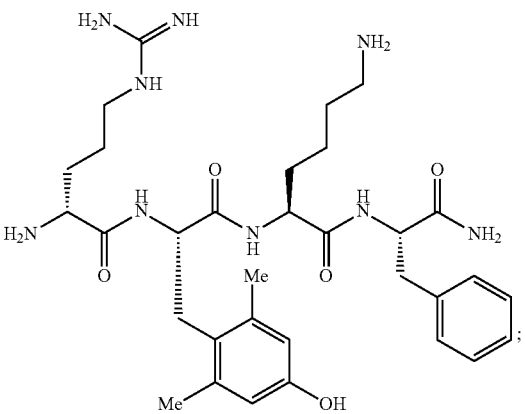

(2)

wherein in formula (1), R is a hydrogen atom, benzyl group, or benzyloxycarbonyl group.

8. The production method according to claim 7, characterized in that compound (1) is produced by condensation via a carbodiimide compound in the presence of a hydroxylamine compound or via a dehydrocondensation agent of Z-D-Arg(Z)2-OH represented by the following formula (3)

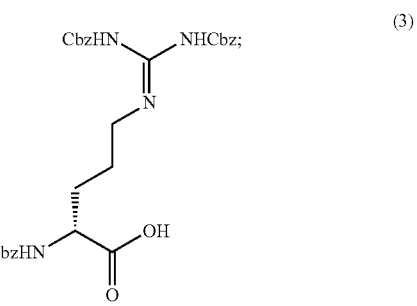

(3)

and the tripeptide compound represented by the following formula (4)

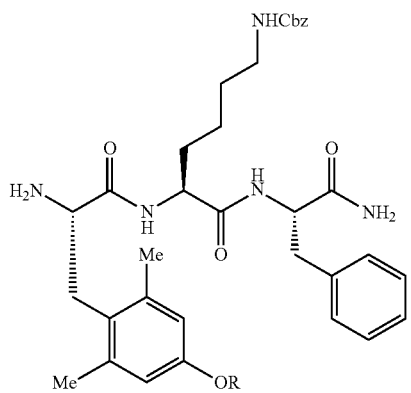

(4)

9. The production method according to claim 7, wherein R is a hydrogen atom.

10. The production method according to claim 7, wherein compound (1) is a solid precipitated from an aprotic polar solvent.

11. The production method according to claim 10, wherein the aprotic solvent is at least one selected from tetrahydrofuran, N,N-dimethylformamide, N,N-dimethylacetamide, N,N-diethylformamide, N,N-dipropylformamide, N,N-dibutylformamide, dimethylsulfoxide, N-methylpyrrolidone, and 1,3-dimethylpropylene urea.

* * * * *